(12) United States Patent
Krieg et al.

(10) Patent No.: US 11,548,036 B2
(45) Date of Patent: Jan. 10, 2023

(54) DEVICE AND METHOD FOR INSPECTING CONTAINERS FOR THE PRESENCE OF FOREIGN MATTER

(71) Applicant: Gunther Krieg, Karlsruhe (DE)

(72) Inventors: Gunther Krieg, Karlsruhe (DE); Juergen Bohleber, Bühl (DE); Dirk Fey, Neewiller (FR); Tobias Frodl, Malsch (DE)

(73) Assignee: Gunther Krieg, Karlsruhe (DE)

( * ) Notice: Subject to any disclaimer, the term of this patent is extended or adjusted under 35 U.S.C. 154(b) by 917 days.

(21) Appl. No.: 16/315,983

(22) PCT Filed: Jul. 5, 2017

(86) PCT No.: PCT/DE2017/200062
§ 371 (c)(1),
(2) Date: Jan. 7, 2019

(87) PCT Pub. No.: WO2018/006910
PCT Pub. Date: Jan. 11, 2018

(65) Prior Publication Data
US 2020/0179986 A1    Jun. 11, 2020

(30) Foreign Application Priority Data
Jul. 6, 2016   (DE) ...................... 10 2016 212 321.1

(51) Int. Cl.
G01N 21/90   (2006.01)
B07C 5/34    (2006.01)
(Continued)

(52) U.S. Cl.
CPC ......... B07C 5/3408 (2013.01); G01N 1/2205 (2013.01); G01N 1/2226 (2013.01);
(Continued)

(58) Field of Classification Search
CPC .. B07C 5/3408; G01N 1/2205; G01N 1/2226; G01N 21/0918; G01N 35/00584;
(Continued)

(56) References Cited

U.S. PATENT DOCUMENTS 5,567,623 A    10/1996   Rounbehler et al.
6,013,228 A    1/2000    Achter et al.

FOREIGN PATENT DOCUMENTS

CN           102854040        * 4/2015
DE    10 2004 034 852 A1       2/2006
(Continued)

*Primary Examiner* — Robert R Raevis
(74) *Attorney, Agent, or Firm* — Seed Intellectual Property Law Group LLP (57) ABSTRACT

Devices and methods for inspecting containers for the presence of foreign matter include, in at least one embodiment, at least one sampling head, at least one pressure sensor, and a filter. The at least one sampling head is configured to introduce an amount of a first fluid into a container and to remove an amount of a second fluid from the container for inspection for the presence of foreign matter. The at least one pressure sensor is configured to measure a pressure of the second fluid upon removal of the second fluid from the container. The filter is arranged in the at least one sampling head and is configured to filter the second fluid.

19 Claims, 5 Drawing Sheets

(51) Int. Cl.
*G01N 1/22* (2006.01)
*G01N 35/00* (2006.01)
*G01N 1/00* (2006.01)

(52) U.S. Cl.
CPC ... *G01N 21/9018* (2013.01); *G01N 35/00584* (2013.01); *G01N 2001/002* (2013.01); *G01N 2001/2291* (2013.01)

(58) Field of Classification Search
CPC ..... G01N 2001/002; G01N 2001/2291; G01N 21/9018
USPC ......... 422/82.05; 73/865.8, 865.9, 865.5, 40, 73/41, 45–45.2, 46, 49.8, 864.33, 864.81; 209/522, 523
See application file for complete search history.

(56) References Cited

FOREIGN PATENT DOCUMENTS

| | | |
|---|---|---|
| DE | 10 2004 048 146 A1 | 4/2006 |
| EP | 0 759 330 A2 | 2/1997 |
| GB | 2 006 430 A | 5/1979 |
| JP | 2010203795 * | 9/2010 |

* cited by examiner

DEVICE AND METHOD FOR INSPECTING CONTAINERS FOR THE PRESENCE OF FOREIGN MATTER

BACKGROUND

Technical Field

The present disclosure relates to devices and methods for inspecting containers for the presence of foreign matter.

Description of the Related Art

The use of plastics in the reusable container sector recently experiences growing importance, in particular in Latin American countries, such as Mexico, etc. Plastic waste already has a significant impact on the environment, whether through the contamination of waters or the ever increasing amount of plastic waste. Nevertheless, plastic bottles are still very popular in the beverage industry, not only because of their significantly lower weight with respect to glass bottles but also because of their robustness. Reusable bottles, i.e., bottles that are filled (again) with beverages and sold several times in the course of their life, are also used by end users in ways not intended. Thus, reusable plastic bottles are also used to temporarily store oil, gasoline, paints, or the like. Due to their conditional elongation at excessive pressure, they also have a lower risk of explosion, etc., compared to glass bottles. Nevertheless, bottles used in this way can also be found again in the recycling loop. Since these bottles may retain the foreign matter contained earlier even after appropriately cleaning the bottle because certain substances are, for example, lipophilic and diffuse into the plastic, these bottles should no longer be used for beverages or food—these substances may, for example, cause an off-taste in case of refilling—and should be reliably rejected.

From DE 10 2004 048 146 A1 is known a device for inspecting containers for the presence of foreign matter. Here, air is blown in via a sampling head and via a compressed air lance after the sampling head is placed on a bottle. Gas can then be removed from the bottle via an extraction line and the extracted gas can be supplied to an analysis system for further examination.

A problem here is that bottles may not only be contaminated with foreign matter but may also have physical damage in the form of holes, edge breaks, or the like, in particular in the area of the bottle opening. If, in this case, the sampling head is placed on and compressed air is blown in, external air may, for example, enter into the bottle via such physical damage and may falsify the measurement result obtained from the extracted gas. In addition, the extracted gas may also escape completely or at least partly from the defect, i.e., not reach or not completely reach the analysis system, which may falsify the measurement result. In this case, contaminated bottles are not sorted out and return to the filling station for refilling with beverages.

BRIEF SUMMARY AND INITIAL DISCLOSURE

The present disclosure relates to a device for inspecting containers for the presence of foreign matter, comprising at least one sampling head, wherein the sampling head can be at least partially placed on the at least one container and an amount of a first fluid can be introduced into the at least one container by means of the sampling head and wherein an amount of a second fluid can be removed from the at least one container by means of the sampling head.

The disclosure further relates to a method for inspecting containers for the presence of foreign matter, comprising the steps of
 a) at least partially placing a sampling head on the at least one container,
 b) introducing an amount of a first fluid into the at least one container by means of the sampling head,
 c) removing an amount of a second fluid by means of the sampling head from the at least one container.

Although applicable in any fields, the present disclosure is explained with respect to multiple use of containers.

Although applicable to any containers, the present disclosure is explained with respect to bottles, reusable bottles, for example.

Although applicable to any foreign matter, the present disclosure is explained with reference to gasoline.

The present disclosure provides various embodiments which may increase reliability in the detection of foreign matters in containers without significantly increasing the manufacturing effort and the costs.

In an embodiment, the present disclosure provides a device for inspecting containers for the presence of foreign matter, comprising at least one sampling head, wherein the sampling head can be placed at least partially on the at least one container and an amount of a first fluid can be introduced into the at least one container by means of the sampling head, and wherein an amount of a second fluid for inspection for the presence of foreign matter can be removed from the at least one container by means of the sampling head, in that at least one pressure sensor is arranged for measuring the pressure, in particular its time profile, of at least the second fluid during its removal from the container.

In another embodiment, the present disclosure provides a method for inspecting containers for the presence of foreign matter, comprising the steps of
 a) at least partially placing a sampling head on the at least one container,
 b) introducing an amount of a first fluid into the at least one container by means of the sampling head,
 c) removing an amount of a second fluid for inspection for the presence of foreign matter by means of the sampling head from the at least one container,
 in that at least the pressure of the second fluid, in particular the time profile of the pressure, is measured by means of at least one pressure sensor during the removal from the container.

The term "foreign matter" is understood to be any substance or any mixture of substances that is not used as intended with respect to the container. For example, in the case of a plastic returnable beverage bottle, the intended or appropriate use of the bottle is limited to the storage of drinkable substances for people without substantial health hazards. Examples of foreign matter plastic returnable beverage bottles are gasoline, oil, urine, lacquers, solvents, etc.

The term "fluid" is to be understood as meaning any substance or mixture of substances which is in a gaseous and/or liquid state of aggregation.

The term "time profile of the pressure" is to be understood as any change in the pressure, in particular an increase and/or a decrease in the pressure, over a predeterminable time. The time profile of the pressure can be present here in the form of a straight line, curve, etc. Furthermore, the analysis of the pressure or pressure profile can be limited to the rising and/or falling edge of the pressure profile.

The term "pressure measurement" is to be understood as any measurement of one or a plurality of pressures. In particular, it is also to be understood as a measurement of a minimum and/or maximum pressure of a time profile of a pressure.

One of the advantages provided by the present disclosure is that monitoring the pressure of the extracted second fluid is possible by means of the pressure sensor so that, for example, when the first fluid is introduced and the second fluid is extracted at the same time, irregular changes in the pressure of the second fluid, which are, for example, due to a hole, broken-off edges, an irregular placing of the sampling head, etc., can be reliably detected in particular based on the time profile of the pressure of the second fluid. Overall, the reliability of the detection of foreign matter in containers is thus substantially increased. Moreover, no substantial additional costs are associated therewith since implementation of at least one pressure sensor is possible in a simple and cost-effective manner.

Further features, advantages, and preferred embodiments of the disclosure are described in, or disclosed by, the following dependent claims.

An analysis device is advantageously arranged for analyzing the pressure of the second fluid measured by means of the at least one pressure sensor and for analyzing the second fluid with respect to foreign matter. A cost-effective implementation of the pressure analysis of the second fluid is thus possible. A separate second analysis device is not required.

The at least one pressure sensor is expediently fluidically arranged downstream of the sampling head and upstream of the analysis device. A particularly precise measurement, in particular close to the sampling head, is made possible by the arrangement between the sampling head and analysis device. Falsifications due to a pressure drop, etc., within the analysis device are thus avoided.

Advantageously, the analysis device is designed to determine foreign matter using one or a plurality of spectroscopic analyses of the second fluid. Spectroscopic analysis of the second fluid enables a fast and at the same time extremely reliable determination of foreign matter in the containers.

A conveyor for the containers is expediently arranged in such a way that the movement of the sampling head and the movement of the containers can be synchronized with one another. In this case, movement of the sampling head and container may, for example, be synchronized electronically or mechanically. Here, for example, in case of a separate drive for the movement of the sampling head, an electronic synchronization device can be arranged in an embodiment. Alternatively, when there is only a geared connection of the sampling head to the drive of the conveyor for the containers, the movement of the container and the movement of the sampling head may be synchronized mechanically, for example, via a gear box. Reliable sampling can thus be carried out in a simple manner.

The sampling head expediently has a sealing body for at least partially sealing the container opening during the introduction of the first fluid and/or during the removal of the second fluid. A sealing body made, for example, from a soft and/or foamed material enables a fluid-tight abutment of the sampling head. In this case, the sampling head or a part of the sampling head can be designed as a spherical inner surface of a wear-resistant hardened stainless steel so that the sampling head can abut the container in a fluid-tight manner in a wide angular range. The latter embodiment permits a low wear of the sealing body and thus a high level of interference resistance.

The sealing body advantageously has a conical hole. The flow of fluids, in particular of the second fluid, in the sampling head can thus be improved. If the second fluid is guided in the region of the container opening in the sampling head guided by holes, this may result in a partial closing of the holes if the sealing body is not entirely planarly resting on the container opening, for example. As a result of the conical design, on the one hand, the sealing surface of the sealing body is as large as possible relative to the container so that a substantially fluid-tight connection is nevertheless made possible even in the case of a not completely planarly positioning. At the same time, the cross-sectional area relative to the sampling head is also as large as possible so that any existing holes are not covered even in the case of a not completely planarly positioning and the flow of the second fluid is thus not impaired.

The sealing body may consist at least partially of rubber. This provides a simple, cost-effective, and reliable seal.

Advantageously, a filter for filtering the second fluid is arranged. It is thus avoided that coarse dirt from the environment, in particular from the container, which is transported along with the second fluid as a result of introducing the first fluid, enters and contaminates the measuring system. This significantly increases the reliability of the device. In addition, a further filter which provides further filtering of the second fluid can be arranged downstream of said first filter, for example in the extraction line. This second filter may be arranged such that a particularly simple maintenance by easy accessibility thereof is made possible.

In at least one embodiment, the filter is expediently arranged in the sampling head. Thus, dirt is already prevented in the sampling head from entering regions, lines, etc., arranged downstream of the sampling head, not just the measuring system.

Advantageously, a fluid supply device is arranged, which is designed to provide the first fluid in the form of a gas or gas mixture. A fluid can be provided in a both simple and reliable manner.

The gas can expediently be supplied by means of the fluid supply device in the form of, in particular oil-free, air. Thus, the fluid can be provided in a particularly easy manner, for example by simply introducing ambient air under pressure into the container.

The pressure sensor is advantageously designed as high-speed pressure sensor. The device can thus be used for a plurality of containers to be inspected, as is required, for example, during the testing of multi-use bottles for purity before refilling, which increases the flexibility with regard to the use of the device.

The response time of the pressure sensor is expediently less than 50 ms in some embodiments. In some embodiments, the response time of the pressure sensor may be less than 25 ms. In some embodiments, the response time of the pressure sensor may be less than 10 ms. In some embodiments, the response time of the pressure sensor may be less than 5 ms. In some embodiments, the response time of the pressure sensor may be between 1 and 3 ms. This permits a fast measurement of the pressure, in particular the time profile of the pressure, so that high clock speeds, i.e., many inspections per time unit of bottles for the presence of foreign matter, are possible such as occur in the recycling of beverage bottles during refilling, for example.

Advantageously, the first fluid can be introduced centrally into the at least one container by means of the sampling head. In this way, a particularly large amount of the second fluid can be reliably introduced from the container into the sampling head in a shorter time and supplied to the later pressure measurement, in particular a measurement of the time profile of the pressure, and analysis.

A sorting device is expediently arranged, which is designed to sort out containers on the basis of a result of the analysis device deviating from a predefined result. In this way, containers for which there is no result or a result deviating from a predefined result can be sorted out in a reliable manner. The predefined result can be calibrated for different residual amounts and different foreign matter by a plurality of containers so that comparing the stored result with the measured result makes possible sorting out the respective container.

Advantageously, in at least one embodiment, the sorting device is designed to supply the containers again at least once to the inspection for the presence of foreign matter. It is thus possible, for example, to take into account the fact that a result deviating from the predefined result does not necessarily justify sorting out. In this case, the container is temporarily sorted out and later inspected again for the presence of foreign matter. In some embodiments, the number of re-inspections can be predetermined. If the result continues to deviate from the predefined result in each or a predefined number, percentage, or the like of the re-inspections, the container can be finally sorted out and, for example, either be removed directly from recycling for the intended use of the container or, if necessary, supplied to a manual control, etc.

In at least one embodiment, air is expediently provided as first fluid. A first fluid can thus be provided in a particularly simple and cost-effective manner.

Advantageously, containers are resupplied at least once to the inspection for the presence of foreign matter when a result of an analysis device deviates from a predefined result during the analysis of the second fluid. In this way, containers for which no result or a result deviating from a predefined result occurs can be sorted out in a reliable manner. The predefined result can be calibrated for different residual amounts and different foreign matter by a plurality of containers so that comparing the stored result with the measured result makes possible sorting out the respective container.

A plurality of containers can expediently be tested simultaneously and the respective pressures of the extracted second fluids can be measured and analyzed simultaneously. This allows for an extremely fast and efficient inspection of containers. The term "simultaneous" with respect to the inspection for the presence of foreign matter is to be understood in particular in the description, preferably in the claims, such that the time period for two or a plurality of inspections for the presence of foreign matter of different containers takes place so quickly that it is essentially insignificant for the time duration of providing further containers. This means, in particular, that a "simultaneous" measurement of pressures also includes a sequential measurement of individual pressures one after the other, wherein the summed time duration of the measurements is substantially smaller than the provision of further new containers for inspection for the presence of foreign matter.

Advantageously, the pressure profile of the second fluid during introduction of the first fluid is measured when the second fluid is extracted. This enables a particularly precise analysis of the pressure and thus also whether, for example, the sampling head has been placed properly on a container.

The pressure, in particular the pressure profile, of the first fluid is expediently measured when it is introduced into the at least one container. This further increases the reliability: If the pressure profile of the first fluid is also measured, it can be determined whether the pressure predetermined for the introduction can be provided.

Advantageously, the pressure profiles of both the first fluid and the second fluid are measured and analyzed. In a particularly reliable manner, a correct placing of the sampling head onto the container can thus, for example, be determined as well as a correct introduction of the first fluid and removal of the second fluid.

The second fluid is expediently examined by optical spectroscopy and the foreign matter is determined by means of the analysis device on the basis of the data obtained from the spectroscopic examination. Thus, both the pressure monitoring and the analysis for foreign matter can, for example, be carried out by means of the analysis device.

The pressure of the second fluid, in particular the pressure profile of the second fluid, is advantageously analyzed by means of the analysis device on the basis of comparing setpoint to actual pressure values, in particular pressure profiles, wherein the inspection of the container can be classified as faulty when a predetermined value is undershot and/or exceeded. An analysis of the pressure of the second fluid can thus be carried out in a simple and simultaneously reliable and fast manner.

The setpoint of the setpoint to actual value comparison is expediently determined based on averaging a plurality of pressure measurements. In this case, the average can be designed as a sliding average, etc., by taking into account only the last 10,000 containers for averaging, for example.

Advantageously, different pressure profiles and/or average values of pressure measurements are analyzed at different points in time. It is furthermore possible to store different pressure profiles or their average values and to analyze them by the analysis device optionally independently of a currently ongoing measurement. For example, if comparing the average pressure value of 10,000 containers from 4 weeks ago with the current average pressure value shows a significant deviation, which can be determined relatively or absolutely in advance, conclusions, for example, can be drawn therefrom regarding contamination of the extraction or supply line, of filters, etc. This then allows timely and nevertheless flexible maintenance of the device as required. Depending on the result of the analysis, maintenance can also be limited to only the filters, purification of the extraction line, etc.

Other important features and advantages of the present disclosure result from the dependent claims, from the drawings, and from the associated description with reference to the drawings.

It goes without saying that the features mentioned above and the features yet to be explained below can be used not only in the respectively specified combinations but also in other combinations or alone, without leaving the scope of the present disclosure.

BRIEF DESCRIPTION OF THE SEVERAL VIEWS OF THE DRAWINGS

Preferred designs and embodiments of the disclosure are shown in the drawings and are explained in more detail in the following description, wherein like reference numerals refer to like or similar or functionally similar components or elements.

DETAILED DESCRIPTION

Figure 1:
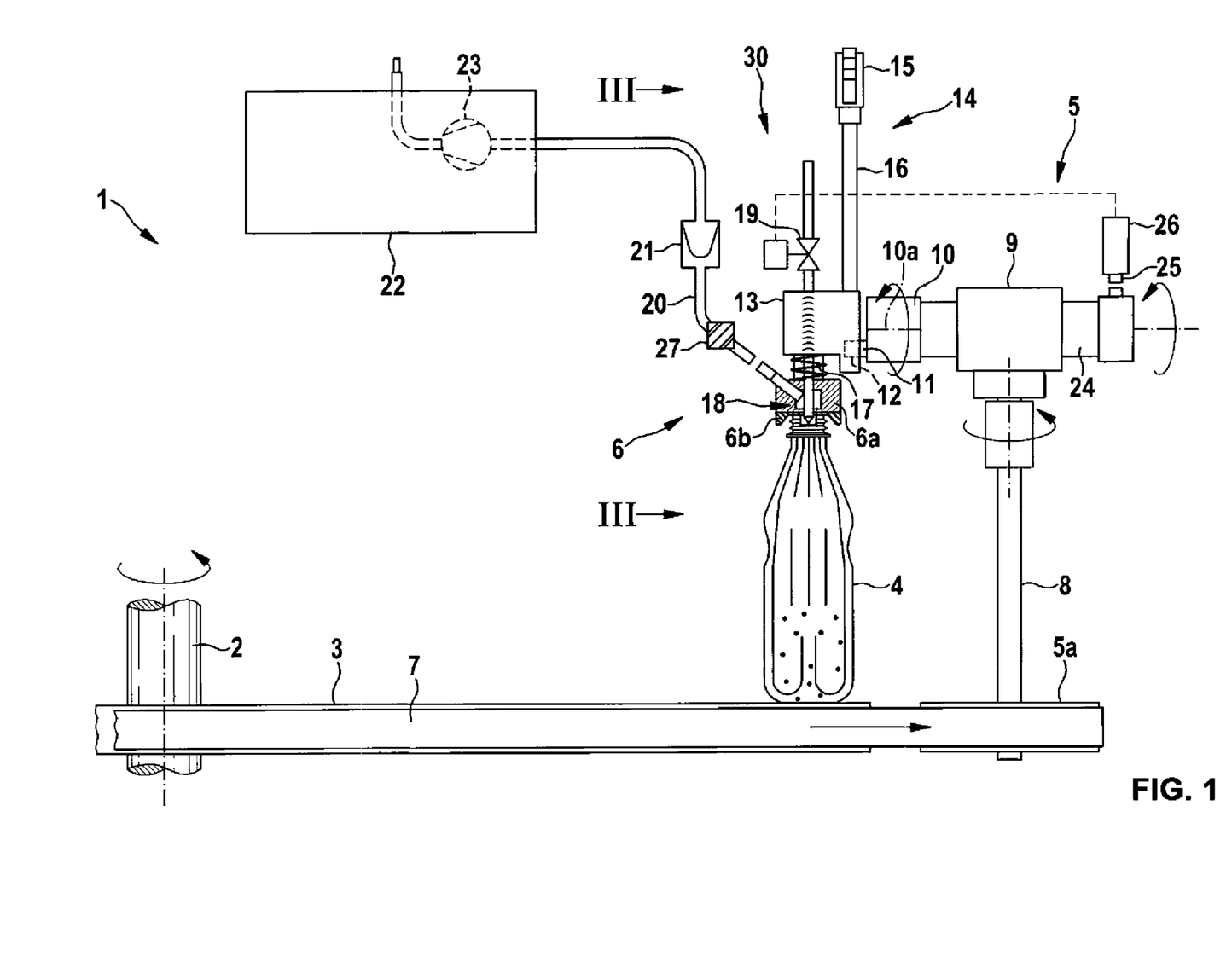
FIG. 1 is a schematic illustration of a device for inspecting containers for the presence of foreign matter, in accordance with an embodiment of the present disclosure in side view.

FIG. 1 schematically shows an illustration of an embodiment of the present disclosure in side view.

In the illustrated exemplary embodiment of FIG. 1, the device 1 according to the disclosure has a circulating conveyor 3 driven by a shaft 2 for containers 4 to be inspected, here refillable PET bottles (REFPET bottles, refillable polyethylene terephthalate bottles). In FIG. 1, the movement of the containers 4 is substantially perpendicular to the plane of the sheet.

Connected to the conveyor 3 is a gear box 5 for actuating a sampling device 6 with a sampling head 6a which is in each case placed on a container 4 for sampling.

In the exemplary embodiment shown, the gear box 5 for driving the sampling device 6 has a drive belt 7 acting on a gear disk 5a. The gear disk 5a is connected to a shaft 8 which acts on an angular gear 9, which is not shown in detail, and to whose output shaft is connected an eccentric 10, which engages with a cam 11 arranged eccentrically to its axis of rotation 10a in a recess 12 (shown by dashed lines) of a holding part 13 in the form of a holding block for the sampling head 6a. The holding part 13 is held and guided via a guide rod system 14.

The guide rod system has a lever 15 pivotally hinged to a fixed point 16. With its other end, it is pivotally connected to a guide rod system 14, which is firmly and rigidly connected to the holding part 13 and guides the latter during its movement caused by the cam 11. The guide rod system shows the circumference of the cam 11 at a constant angular velocity. The non-uniform horizontal movement of the articulation point of the rod system 14 on the holding part 13 is largely compensated with respect to the sampling head 6a so that it can follow the movement of the containers.

The sampling head 6a is arranged resiliently or movably toward the guide rod system 16 on the holding part 13, for example by a coil spring 17, wherein it may also have a certain angular flexibility with respect to the holding head 13.

First, a compressed air lance 18, the compressed air supply of which can be controlled via a valve 19, leads into the sampling head 6a. Furthermore, a sampling tube 20, which is connected to a measuring system 22 via a filter 21 filtering out solid and liquid parts, enters into the upper region of the sampling head 6a. A suction pump 23 is not necessarily but advantageously provided in the sampling tube system.

On the side of the angular gear 9 facing away from the eccentric 10, there is a further output shaft 24, which has on its circumference a switch cam 25 which controls the valve 19 in the compressed air lance 18 via an associated pulse generator 26.

The position in which the holding part 13 and thus the sampling head 6a is located at its uppermost location is referred to as 0° position, while the position in which the holding part 13 and thus the sampling head 6a is pushed downward as far as possible is referred to as 180° position. In the 0° position, the horizontal association of sampling head 6a and container in the direction of movement of the containers is such that the sampling head is located approximately centrally between two opposing containers.

The movements of the container 4 and the component extending parallel thereto (horizontal component) of the holding part 13 and thus of the sampling head 6a are synchronized with one another, in the illustrated exemplary embodiment by means of the described gear box and guide rod system, so that both movements substantially correspond in their speed and direction.

A container 4 reaches with its opening below the sampling head 6a the 90° position thereof. At 105°, the lower edge of the sampling head 6a engages around the upper edge of the container 4. At about 120°, the seal or sealing body 6b of the sampling head rests on the upper edge of the sampling head 6a on the upper edge of the container. At this movement phase, the switch cam 25 also reaches the pulse generator 26 and thus, by opening the valve 19, triggers a compressed air pulse via the nozzle of the compressed air lance 18 into the container, as a result of which the gas present therein is guided via the sampling line 20 to the measuring system 22.

In the event of further movements to 180°, the holding block 13 moves further downward, while the sampling head 6a is prevented from further movement downward by the upper edge of the container 4. As a result of the elastic connection between the sampling head 6a and the holding part 13, the latter presses the sampling head 6a firmly against the upper edge of the container.

At 180°, as stated, the holding part 13 reaches its lowest position and thus exerts the greatest pressing force on the sampling head 6a.

The sample is analyzed in the measuring system 22, for example spectroscopically by means of UV or IR light or by means of microwave radiation, although other measuring methods such as mass spectrometry or the so-called TOF (time of flight) technique can also be used, wherein an ionization of the gas driven out of the container 4 and acceleration of the gas molecules in the electric field takes place and the gas types are determined from the flight times resulting over a predetermined distance.

With the further movement beyond the 180° position, the holding block 13 is raised off the container 4 again and thereby detaches the sampling head 6a from the container opening, wherein the sampling head 6a releases the top of the container 4 completely at the latest at 270° so that the container can be freely conveyed further by the conveyor 2, while the holding block 13 and thus the sampling head 6a is returned into the 0° position and, after renewed lowering to the 90° position, is brought again above the opening of the next container so that gas can be extracted for inspection from said container in the manner described.

At least one embodiment of the present disclosure comprises a sampling head 6a having a sealing body 6b which is designed in such a way that its curved sealing surface abutting the container opening is formed convex in cross section toward the inside and toward the container opening. The sealing surface corresponds in particular to that of an inner sectional view of a sphere. This reliably ensures a fluid-tight abutment of the sealing body 6b on the container 4 over a wide angular range. This sealing body 6b includes a nearly wear-resistant, hardened material, such as stainless steel, so that it is subject to low wear and thus provides low susceptibility to interference. Advantageously, the compressed-air lance 18 advantageously moves into the container 4 when the sampling head 6a is placed on the container 4, i.e., only the sealing sampling head 6a rebounds, while the compressed air lance 18 follows exactly the movement of the eccentric 10.

Figure 2:
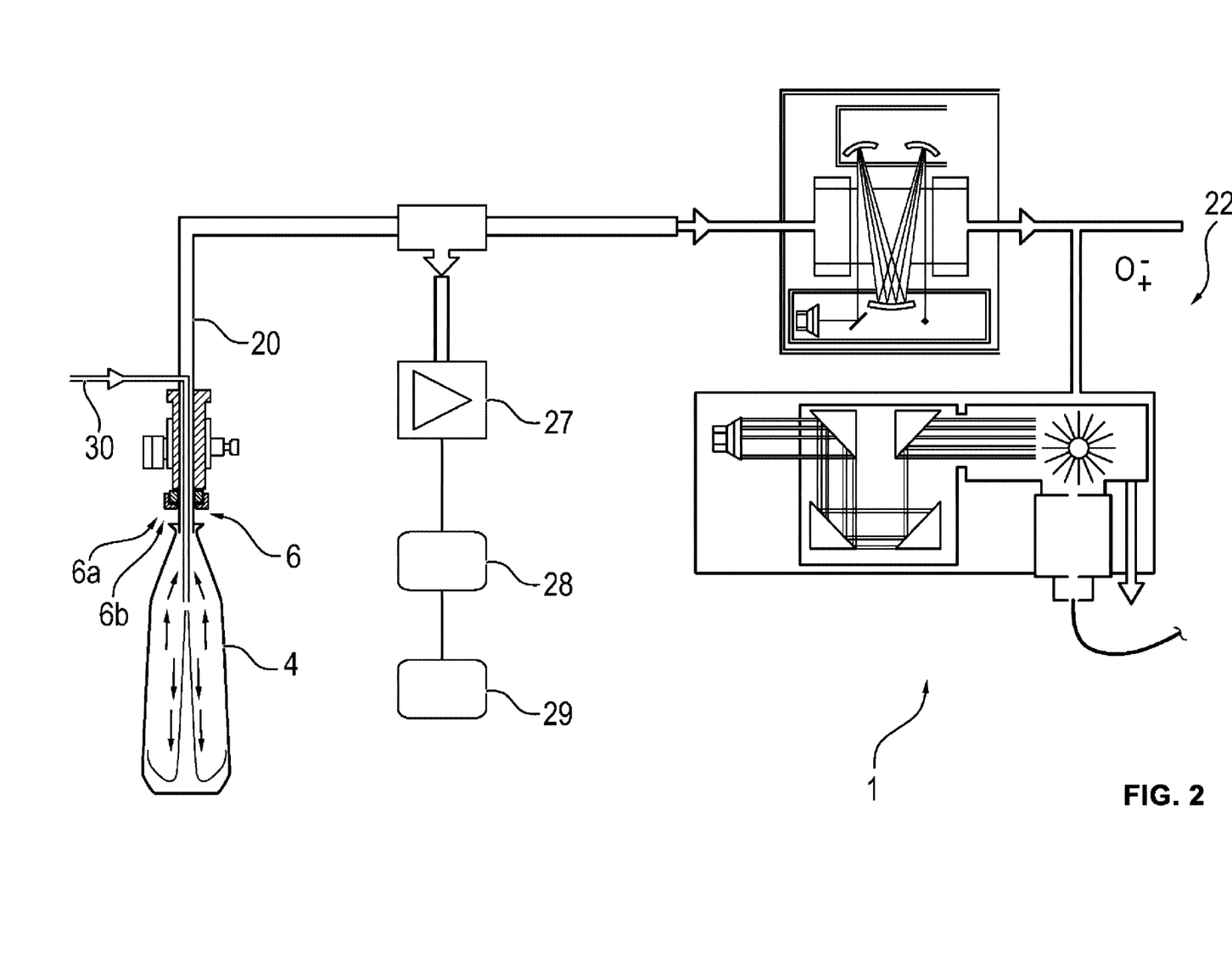
FIG. 2 is a schematic illustration of some features of a device for inspecting containers for the presence of foreign matter, according to a further embodiment of the present disclosure.

FIG. 2 shows a basic structure of a device according to a further embodiment of the present disclosure.

In FIG. 2, a device 1 is shown essentially according to FIG. 1. Air is blown into the container in the form of a bottle 4 via the compressed-air supply line 30 after the sampling head 6 has been placed on the container opening. The gas escaping in bottle 4 as a result of placing or blowing in compressed air is supplied via an extraction line 20 to a high-speed pressure sensor 27 connected to a data collection device 28. The data collection device 28 is connected to an analysis device 29 for analyzing the data obtained. Optionally, the data collection device 28 processes the raw data of the pressure sensor 27 for the analysis device 29, which may also be connected to the measuring system 22. Furthermore, the extraction line 20 is connected to the measuring system 22 which, for example, inspects the second fluid by means of spectroscopic analysis. The analysis device 29 and/or the data collection device 28 can also be part of the measuring system 22. Based on the result of the pressure sensor 27, it can be distinguished whether the measurement process was reliably performed or whether, for example, a leak may lead to falsifications in the analysis of the second fluid by the measuring system 22.

Figure 3:
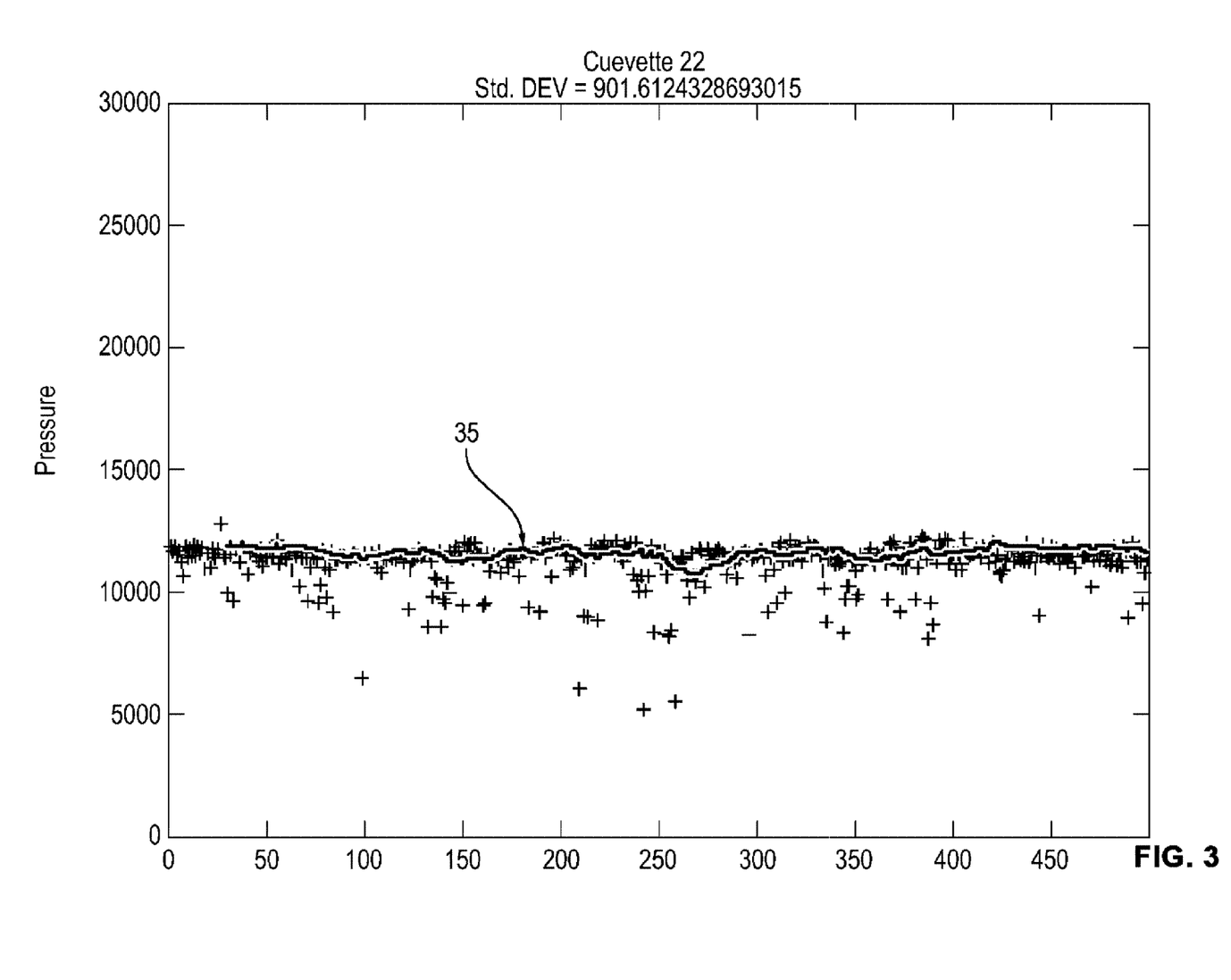
FIG. 3 is a graph showing results of a pressure measurement of 1.5 liters REFPET bottles at a speed of 36,000 bottles per hour over a period of 30 minutes.

FIG. 3 shows results of a pressure measurement of 1.5-liter REFPET bottles at a speed of 36,000 bottles per hour over a period of 30 minutes.

FIG. 3 shows a pressure measurement of a plurality of 1.5-liter REFPET bottles. In this case, 36,000 bottles are inspected per hour by the device. As can be seen, defective bottles which possibly falsify the measurement result can be detected by a significant pressure drop from the average or from the main line 35 in the range of about 11,000 (arbitrary unit). Individual measurements are less than half of said average pressure. Pressure measurements below the main line 35 correspond to a pressure that is too low for successful sampling of the second fluid. The corresponding containers are sorted out then, optionally re-supplied to one or a plurality of measurements, for example, by guiding them back to the entry of device 1 according to FIG. 1 or by finally sorting out after unsuccessful, repeated measurement.

Figure 4:
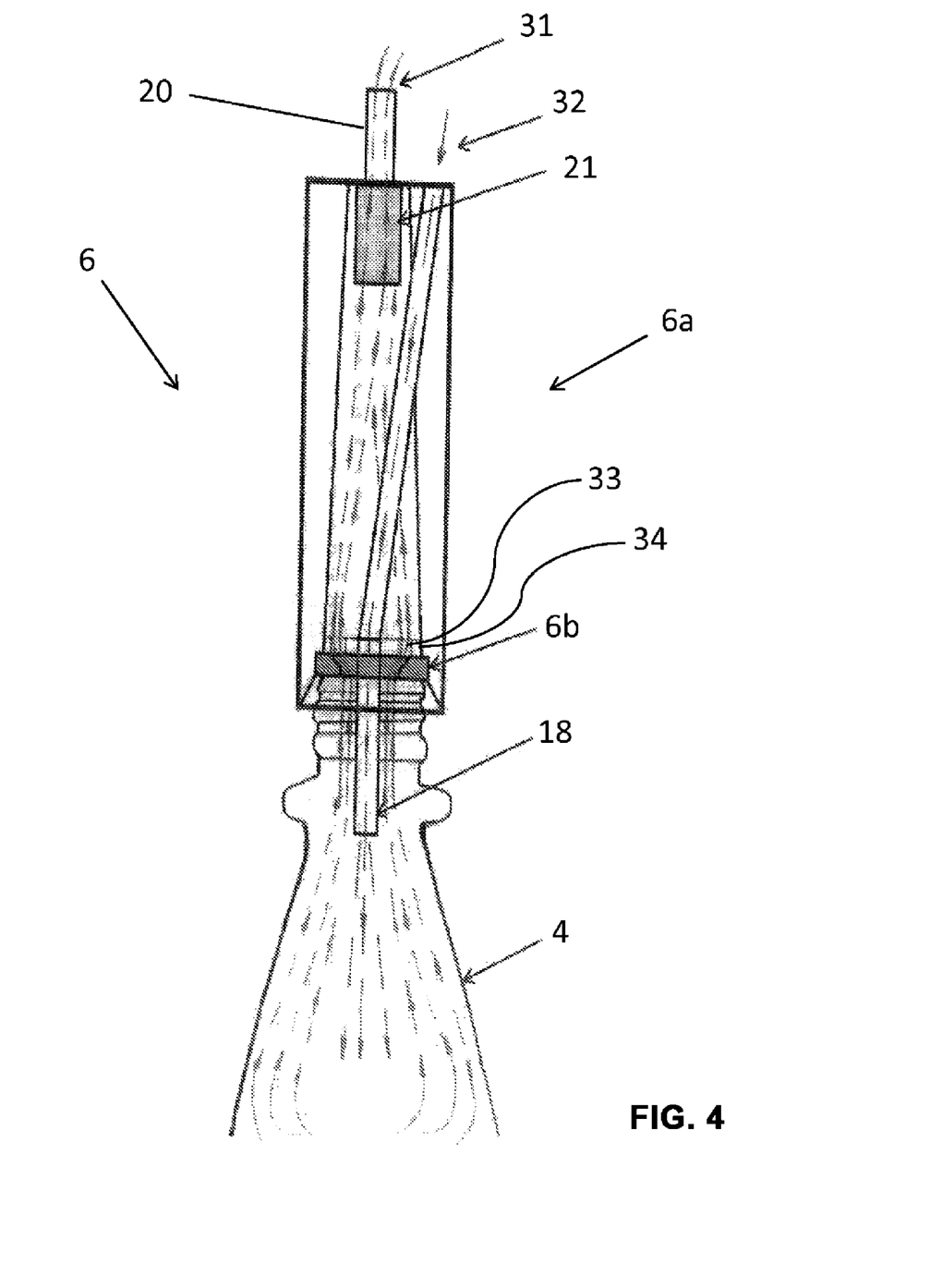
FIG. 4 is a schematic illustration of a section of a device in the region of the sampling head, in accordance with a further embodiment of the present disclosure.

FIG. 4 shows a section of a further embodiment of the present disclosure in the region of the sampling head in a schematic illustration.

FIG. 4 shows essentially a sampling device 6 with a sampling head 6a in the state placed on a PET bottle 4. In order to seal the transition between the sampling head 6a and the PET bottle 4 toward the environment, the sampling head 6a has a seal 6b so that a substantially fluid-tight connection between the sampling head 6a and the PET bottle 4 is made possible. This seal 6b is designed in the form of a sealing ring with conical opening, wherein this opening tapers toward the opening of the PET bottle 4.

The sampling head 6a comprises a fluid line for introducing a fluid, here in the form of a compressed air lance 18 for blowing in, in particular oil-free, air. The compressed air lance may extend into the widening region of the PET bottle 4 for blowing in air 32. The compressed air lance 18 is fixed in the sampling head 6a by means of a fixing ring 34, here essentially in the center of the opening of the sampling head facing the PET bottle 4. In the circumferential direction, the fixing ring 34 has holes 33 for the passage of the second fluid, here the displaced air 31. The compressed air lance 18 is guided through the opening of the seal (sealing ring) 6b; the radial arrangement of the holes corresponds to the widening opening of the sealing ring 6b, in particular such that the maximum radial extent of the holes 33 from the center of the sealing ring 6b or fixing ring 34 corresponds to the maximum expansion of the sealing ring 6b as shown in FIG. 4 and the holes can be completely impinged upon by a fluid passing through the sealing ring 6b.

If air 32 is now blown into the container 4 via the compressed air lance 18, an excess pressure develops in the container 4 and the air 31 displaced by the blown-in air 32 escapes via the opening of the container 4, passes through the sealing ring 6b into the sampling head 6a, and also passes a filter 21 arranged on the side of the sampling head 6a facing away from the container 4, and passes into an extraction line 20 which is connected to a high-speed pressure sensor 27 for measuring the pressure of the displaced air 31 and to one or a plurality of measuring systems 22.

Figure 5:
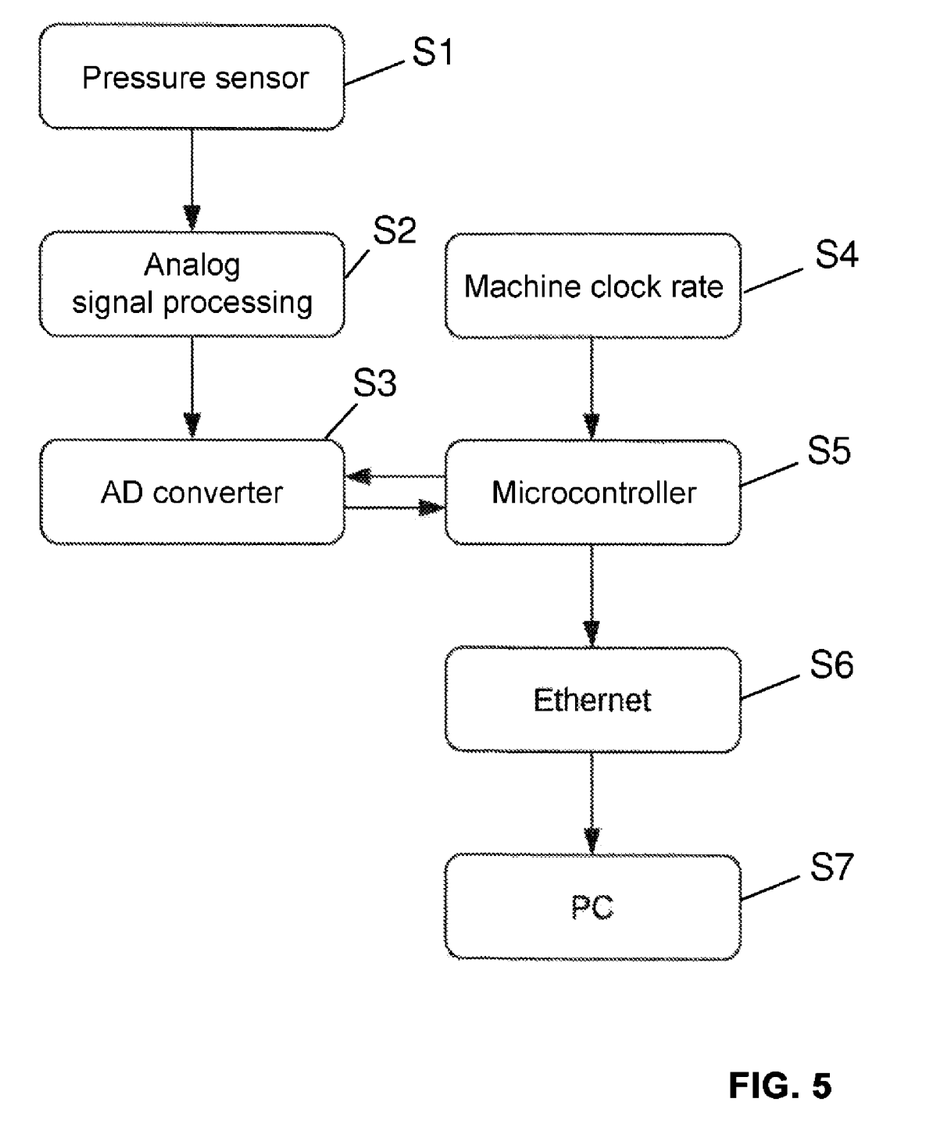
FIG. 5 is a flowchart illustrating a method according to an embodiment of the present disclosure.

FIG. 5 shows parts of a method according to an embodiment of the present disclosure.

FIG. 5 essentially shows the following steps: In a first step S1, a pressure sensor measures the pressure of the second fluid.

In a second step S2, the signal of pressure output by the pressure sensor is processed in an analog manner, for example amplified, smoothed, or the like. In addition, a plurality of signals may be summed up or the like.

In a third step S3, the processed signal is supplied to an analog/digital converter and converted into a digital signal.

In a fourth step S4, the digital signal is processed by a microcontroller, that also contains data, in particular the clock rate of a machine, such as a conveyor and sorting device for PET bottles for supplying and conveying away containers for the measurement of ingredients in a further step S5. If further data, for example of other measuring parameters, are provided by the analog/digital converter, the microcontroller can communicate with the analog/digital converter and select corresponding data for transmission to it. Prior to forwarding the digital data of the pressure sensor, the microcontroller may synchronize them with the machine clock rate so that the pressure measurements can be assigned unambiguously to a given PET bottle. For example, a delay in the forwarding of the digital data of the pressure sensor may take place if the working clock rate of the inspection of the PET bottles has changed in the meantime. Furthermore, the microcontroller is connected, for example via Ethernet, to an industrial personal computer which performs, in a further step S7, an analysis of the measured pressure and machine clock rate. Thus, for example, in case of deviations of the pressure from a predetermined value, the respective PET bottle can also be identified based on the machine clock rate during the further course of the transport and can be optionally returned to the entry of the device for a new measurement or can also be directly sorted out. The industrial PC can, for example, carry out a threshold value check by comparing the measured value provided by the microcontroller with a threshold value and, in case of falling below or exceeding the threshold value, a corresponding signal can then be output automatically, the device can be stopped, or the like.

In summary, the present disclosure has the advantage that the reliability in the detection of foreign matter is substantially increased by means of the pressure sensor and an analysis of the pressure of the extracted fluid.

Although the present disclosure was described with reference to preferred exemplary embodiments, it is not limited thereto but modifiable in a variety of ways.

LIST OF REFERENCE SYMBOLS

1 Device
2 Shaft

3 Circular conveyor
4 Container
5 Gear
5a Gear disk
6 Sampling device
6a Sampling head
6b Seal
7 Pulse generator
7 Drive belt
8 Shaft
9 Angular gear
10 Eccentric
10a Axis of rotation
11 Cam
12 Recess
13 Holding part
14 Guide rod system
15 Lever
16 Guide rod system
16a Fixed point
17 Coil spring
18 Compressed air lance
19 Valve
20 Sampling tube, extraction line
21 Filter
22 Measuring system
23 Suction pump
24 Output shaft
25 Switch cam
26 Pulse generator
27 High-speed sensor
28 Data collection, data analysis
29 Analysis device
30 Compressed-air supply line
31 Air flow of displaced air
32 Air flow of blown-in air
33 Hole
34 Fixing ring
35 Main line
S1-S7 Method steps The various embodiments described above can be combined to provide further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A device for inspecting containers for the presence of foreign matter, comprising:
at least one sampling head configured to introduce an amount of a first fluid into a container, and to remove an amount of a second fluid from the container for inspection for the presence of foreign matter;
at least one pressure sensor configured to measure a pressure of the second fluid upon removal of the second fluid from the container;
a filter configured to filter the second fluid, wherein the filter is arranged in the at least one sampling head; and
an analysis device configured to analyze the second fluid to determine a presence of foreign matter in the second fluid,
wherein the device is configured to resupply the at least one container to the at least one sampling head for inspection for the presence of foreign matter in response to a result of the analysis device from the analysis of the second fluid deviating from a predefined result.

2. The device according to claim 1,
wherein the analysis device is communicatively coupled to the at least one pressure sensor and configured to analyze the measured pressure of the second fluid, the device further comprising:
a sorting device configured to sort out the container in response to the result of the analysis device deviating from the predefined result.

3. The device according to claim 2, wherein the at least one pressure sensor is fluidically arranged downstream of the at least one sampling head and upstream of the analysis device.

4. The device according to claim 2, wherein the analysis device is configured to determine the presence of foreign matter by performing a spectroscopic analysis of the second fluid.

5. The device according to claim 1, further comprising a conveyor configured to convey the container from a first position to the at least one sampling head, and from the at least one sampling head to a second position that is different from the first position, wherein movements of the container and the at least one sampling head are synchronized with one another.

6. The device according to claim 1, wherein the at least one sampling head includes a sealing body configured to at least partially seal an opening of the container during at least one of the introduction of the first fluid or the removal of the second fluid, wherein the sealing body includes a conical hole and is formed at least partially of rubber.

7. The device according to claim 1, further comprising a fluid supply line configured to supply the first fluid in the form of a gas or a gas mixture, wherein the gas includes air.

8. The device according to claim 1, wherein the at least one pressure sensor is a high-speed pressure sensor having a response time of less than 50 ms.

9. The device according to claim 8, wherein the response time of the high-speed pressure sensor is less than 10 ms.

10. The device according to claim 1, wherein the at least one sampling head is configured to introduce the first fluid centrally into the container.

11. The device according to claim 1, wherein the device is configured to simultaneously inspect a plurality of containers and to simultaneously measure respective pressures of second fluids removed from the plurality of containers.

12. A method for inspecting containers for the presence of foreign matter, comprising:
at least partially positioning a sampling head on at least one container;
introducing an amount of a first fluid into the at least one container by way of the sampling head;
removing an amount of a second fluid for inspection for the presence of foreign matter from the at least one container by way of the sampling head;
measuring, by at least one pressure sensor, a pressure of the second fluid removed from the at least one container;
filtering, by a filter, the second fluid removed from the at least one container;
analyzing, by an analysis device, the second fluid removed from the at least one container to determine a presence of foreign matter in the second fluid; and
resupplying the at least one container to the sampling head for inspection for the presence of foreign matter in response to a result of the analysis device from the analysis of the second fluid deviating from a predefined result.

13. The method according to claim 12, wherein the first fluid includes air.

14. The method according to claim 12, wherein a pressure profile of the second fluid during the introduction of the first fluid is measured when the second fluid is removed.

15. The method according to claim 14, further comprising:
measuring a pressure profile of the first fluid during the introduction of the first fluid into the at least one container.

16. The method according to claim 15, further comprising analyzing the pressure profiles of both the first fluid and the second fluid.

17. The method according to claim 12, wherein the second fluid is analyzed by optical spectroscopy and the presence of foreign matter is determined by the analysis device based on data obtained from the optical spectroscopic analysis.

18. The method according to claim 14, wherein the analysis of the second fluid includes analyzing the pressure profile of the second fluid by comparing the pressure profile with a setpoint of pressure values, the method further comprising:
classifying the at least one container as faulty in response to a result of the comparison falling below or exceeding a predetermined pressure value,
wherein the setpoint is set by averaging a plurality of pressure measurements.

19. The method according to claim 18, wherein different pressure profiles or average values of pressure measurements are analyzed at different points in time.

* * * * *